(12) United States Patent
Araki

(10) Patent No.: US 7,547,688 B2
(45) Date of Patent: Jun. 16, 2009

(54) METHODS FOR TREATMENT OF NOCTURIA

(75) Inventor: Tohru Araki, Okayama (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 11/906,564

(22) Filed: Oct. 3, 2007

(65) Prior Publication Data

US 2008/0090910 A1    Apr. 17, 2008

Related U.S. Application Data

(60) Division of application No. 11/471,340, filed on Jun. 20, 2006, now abandoned, which is a continuation of application No. 10/242,754, filed on Sep. 13, 2002, now abandoned.

(51) Int. Cl.
*A61K 31/33*    (2006.01)
*A61K 31/192*   (2006.01)

(52) U.S. Cl. .................. 514/183; 514/570; 514/529

(58) Field of Classification Search ............... 514/183, 514/570
See application file for complete search history.

(56) References Cited

U.S. PATENT DOCUMENTS 6,297,260 B1   10/2001   Bandarage et al.
6,569,860 B2    5/2003   Lopez-Tapia et al.

FOREIGN PATENT DOCUMENTS

WO   WO 02/11707 A2    2/2002
WO   WO 02/47661 A1    6/2002
WO   WO 02/070514 A1   9/2002

OTHER PUBLICATIONS

Kimura et al., Clinical and Experimental Dermatology, vol. 22, Issue 6 (p. 303-304) 1997.*
Al-Waili, *IRCS Medical Science*, vol. 14, pp. 322-323, 1986.
Resnick et al., *Campbell's Urology*, 7th Edition, vol. 2, Chapter 31, Philadelphia: Saunders, 1998, pp. 1044-1058.
Suzuki S., *Acta. Urol. Jpn.*, vol. 43, pp. 402-403, 1997.
*Remington's Pharmaceutical Sciences*, Mack Publishing Co., 1975, 15th Edition, p. 378.
Al-Waili, "Diclofenac Sodium in the Treatment of Primary Nocturnal Enuresis: Double-Blind Crossover Study," *Clinical and Experimental Pharmacology & Physiology*, (1986), 13, pp. 139-142.
Kawai et al., "Comparison of cyclooxygenase-1 and 2-inhibitory activities of various nonsteroidal anti-inflammatory drugs using human platelets and synovial cells," *European Journal of Pharmacology*, 347 (1998), pp. 87 to 94.

* cited by examiner

*Primary Examiner*—Ardin Marschel
*Assistant Examiner*—Donna Jagoe
(74) *Attorney, Agent, or Firm*—Frishauf, Holtz, Goodman & Chick, P.C.

(57) ABSTRACT

A method for the treatment of nocturia which consists of administering to a mammal in need of such treatment a therapeutically effective amount of a nonsteroidal anti-inflammatory drug consisting of loxoprofen or a pharmacologically acceptable salt thereof, wherein the mammal has a neurogenic bladder.

2 Claims, No Drawings

METHODS FOR TREATMENT OF NOCTURIA

CROSS-REFERENCE TO RELATED APPLICATIONS

This application is a divisional application of application Ser. No. 11/471,340 filed Jun. 20, 2006 now abandoned, which is a continuation application of application Ser. No. 10/242,754 filed Sep. 13, 2002 (abandoned).

FIELD OF THE INTENTION

The present invention relates to a preventive and/or therapeutic treatment of nocturia.

RELATED ART

Lower urinary tract symptoms (LUTS) are becoming a major health problem for elderly people worldwide. Nocturia, a cause of insufficient sleep and thus impaired quality of life, is one of the main problems in LUTS along with urinary incontinence and difficulty in urination. The aetiology of nocturia is various and complex and obscure in many patients, although LUTS, insomnia, nocturnal polyuria due to cardiovascular or renal hypofunction and disorders of the central nervous system (CNS) may be among the causes (Resnick N. M., et al., *Campbell's Urology*, 7$^{th}$ edn, Vol. 2. Chapt. 31. Philadelphia: Saunders, 1998: 1044-58).

The aetiology of nocturia is still obscure in many patients, even in those with BPH. In patients whose causes of nocturia are affirmable, such as those with LUTS, sleep disorder and nocturnal polyuria, nocturia may be improved by effective treatment of these primary causes. Anticholinergic drugs, hypnotics, antidiuretic hormone, Chinese herbal medicines and/or oestrogen for female patients are usually administered for nocturia in addition to treatments for their main diseases. However, in the inventor's experience, about one-half of such patients do not respond well to these medications.

As for effectiveness of nonsteroidal anti-inflammatory agents for treatment of frequent of micturition, Al-Waili reported that in an open trial indomethacin 100 mg suppository improved nocturia in all 15 patients (Al-Waili, IRCS Med. Sci., 1986, 14, 322-3). In addition, Suzuki reported a patient whose nocturia was improved with indomethacin suppository administered as antipyretics, and added a brief comment that some orally administered NSAIDs are also effective in nocturia (Suzuki S., Acta Urol. Jpn., 43, 402, 1997).

DISCLOSURE OF THE INVENTION

An object of the present invention is to provide a medicament which is effective for treatment of nocturia.

The inventor has surprisingly experienced that a patient who was being treated for BPH reported that his nocturia suddenly decreased from a usual of four voids to one void/night when he took a 60-mg tablet of loxoprofen sodium (loxoprofen) prescribed for his shoulder pain before sleeping. Based on the experience, the inventor conducted a non-randomized trial treatment with loxoprofen, a short-acting nonsteroidal anti-inflammatory drug (NSAID) prodrug usually prescribed at a dosage of 60 mg t.i.d. for the management of pain, in patients bothered by nocturia. As a result, the inventor found that loxoprofen was surprisingly effective for treatment of nocturia. The inventor also found that a class of nonsteroidal anti-inflammatory drugs are also effective for treatment of nocturia. The invention was achieved on the basis of these findings.

The present invention thus provides a medicament for preventive and/or therapeutic treatment of nocturia, which comprises a nonsteroidal anti-inflammatory drug as an active ingredient.

The present invention also provides a method for preventive and/or therapeutic treatment of nocturia, which comprises the step of administering to a mammal including a human in need of such treatment a preventively and/or therapeutically effective amount of a nonsteroidal anti-inflammatory drug, and a use of a nonsteroidal anti-inflammatory drug for manufacture of the aforementioned medicament which comprises said nonsteroidal anti-inflammatory drug as an active ingredient.

Among a class of nonsteroidal anti-inflammatory drugs, a class of phenylpropionic acid-type anti-inflammatory drugs are preferred, and loxoprofen is particularly preferred.

BEST MODE FOR CARRYING OUT THE INVENTION

Kinds of the nonsteroidal anti-inflammatory drugs as an active ingredient of the medicament of the present invention are not particularly limited. Any nonsteroidal anti-inflammatory drug can be used alone or in combination as the active ingredient of the medicament of the present invention. The term "nonsteroidal anti-inflammatory drug" used herein means an anti-inflammatory drug which does not have a steroidal backbone structure, and the scope of the nonsteroidal anti-inflammatory drugs is readily apparent to one of ordinary skill in the art. Accordingly, the term should not be construed any limiting sense and should be understood in the broadest sense. In addition, the term "nonsteroidal anti-inflammatory drug" used herein encompasses a drug in a free form, as well as a pharmacologically acceptable salt thereof, a hydrate thereof, or a solvate thereof. Any stereoisomer such as an optical isomer or a diastereoisomer, or any mixture of the stereoisomer or a racemate of the nonsteroidal anti-inflammatory drug may be used. Any novel nonsteroidal anti-inflammatory drugs as well as any clinically available nonsteroidal anti-inflammatory drugs may be used as active ingredients of the medicament of the present invention. Preferred class of nonsteroidal anti-inflammatory drugs include phenylpropionic acid-type anti-inflammatory drugs.

Examples of the nonsteroidal anti-inflammatory drugs include aspirin, lumiracoxib, etoricoxib, parecoxib, valdecoxib, tiracoxib, rofecoxib, celecoxib, darbufelone, dexketoprofen, aceclofenac, licofelone, bromfenac, pranoprofen, piroxicam, nimesulide, cizolirine, ketorolac, 3-formylamino-7-methylsulfonylamino-6-phenoxy-4H-1-benzopyran4-one, ibuprofen, meloxicam, lornoxicam, d-indobufen, mofezolac, nabumetone, amtolmetin, droxicam, pranoprofen, ketoprofen, tolfenamic acid, fenoprofen, flurbiprofen, suprofen, oxaprozin, loxoprofen, tenoxicam, zaltoprofen, ibuprofen, alminoprofen, and tiaprofenic acid, and pharmacological salt thereof, hydrate thereof, and solvate thereof. However, the nonsteroidal anti-inflammatory drugs are not limited to these examples. Among them, loxoprofen and a pharmacological salt thereof is preferred, and loxoprofen sodium is more preferred.

The medicament of the present invention may be administered orally or parenterally to a patient with nocturia. When a clinically available nonsteroidal anti-inflammatory drug is used as an active ingredient of the present invention, the available drug, per se, may be administered to a patient with nocturia as the medicament of the present invention. Alternatively, a pharmaceutical composition may be administered to a patient which comprises at least one nonsteroidal anti-inflammatory drug as the active ingredient together with at least one pharmaceutically acceptable additive. The pharmaceutical composition can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, suppositories, inhalants, eye drops, nasal drops, ointments, creams, patches and the like.

The aforementioned pharmaceutical compositions may be prepared by the addition of pharmaceutically acceptable additives to the active ingredient. Examples of pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like.

A dose of the medicaments of the present invention is not particularly limited, and the dose can suitably be selected depending on conditions such as, for example, route of administration, the age and body weight of a patient, symptoms, a purpose of preventive or therapeutic treatment and the like. For example, for oral administrations, the medicament of the present invention may be administered in a dose of from 0.1 to 1,000 mg per day, preferably 1 mg to 100 mg for an adult The medicament of the present invention may be administered once or several times a day, and preferably, the medicament may be administered once before sleeping. For example, when loxoprofen is administered as the medicament of the present invention, a dose of 60 mg per day is preferred, and the dose may preferably be administered once before sleeping. However, the dose and mode of administration is not limited to the above example.

EXAMPLE

The present invention will be explained more specifically by way of examples. However, the scope of the present invention is not limited to these examples.

Patients and Methods

One hundred forty one patients (136 men) aged 49 to 89 (mean 70.5) years with LUTS and =2 voids per night were enrolled in the study. Their main diseases were BPH (n=93), prostate cancer(n=24) and neurogenic bladder (NB) (n=13); 11 had other diseases. The majority of patients had failed to respond to anticholinergic drugs, hypnotics and/or other medications for nocturia prescribed in addition to their treatments for their main diseases. Patients who had asthma, gastrointestinal disorders, renal dysfunction and allergies to loxoprofen were excluded.

Patients took a single 60 mg loxoprofen tablet prior to sleeping at night for 4 to 14 days initially concurrently with their treatments for their main diseases. Numbers of voids/ night as reported by each patient were evaluated and treatment outcome was assessed as either excellent (nocturia disappeared or decreased by =2 voids/night), improved (nocturia decreased by 1 void/night), unchanged or worsened (nocturia increased).

After the initial study, loxoprofen was administered at the patients' discretion; 101 continued loxoprofen therapy for =320 (mean 61) days.

Results

Changes in patients' symptoms were observed starting from the first night of therapy. Nocturia improved or disappeared in 72% of the patients overall: excellent, improved, unchanged and worsened results were obtained in 36%, 36%, 24% and 4%, respectively (Table 1).

TABLE 1

Effects of loxoprofen in 141 patients with nocturia

|  | No. of Patients | Excellent | Improved | Unchanged | Worsened |
|---|---|---|---|---|---|
| Male, | 135 | 49 (36%) | 48 (36%) | 32 (24%) | 6 (4%) |
| Female, | 6 | 2 (33%) | 2 (33%) | 2 (33%) | — |
| Total | 141 | 51 (36%) | 50 (36%) | 34 (24%) | 6 (4%) |

Patients whose nocturia improved generally reported noticeable improvements in their quality of life through having sound sleep. Even in the unchanged group, some patients reported sleeping better than they did prior to treatment because the time to first voiding was delayed by several hours.

Loxoprofen's effects were analyzed on the basis of frequency of nocturia at baseline (Table 2). The effects were better in patients whose baseline frequency was >3 voids/ night than in those with less-frequent nocturia: when the patients were divided into 2 groups, 56 with 2 to 3 episodes of nocturia and 85 with more frequent nocturia, the excellent responder rates were 21% and 46% in each, respectively (P=0.004, Fisher's exact test). The excellent responder rates slightly reduced with increased age of patients: excellent responses were observed in 50% (4/8) of patients aged 49 to 59 years, 40% (17/43) in those aged 60 to 69 years, 35% (23/65) in those aged 70 to 79 years, and 28% (7/25) in those aged 80 to 86 years.

TABLE 2

Effects of loxoprofen vs frequency of nocturia at baseline

| Frequency at Baseline | No. of Patients | Excellent | Improved | Unchanged | Worsened |
|---|---|---|---|---|---|
| 2 and 2-3 | 56 | 12* (21%) | 23† (41%) | 19† (34%) | 2 (4%) |
| 3-4 | 59 | 28† (47%) | 18† (31%) | 10† (17%) | 3 (5%) |
| 4-5 | 15 | 6 (40%) | 6 (40%) | 3 (20%) | — |
| >5 | 11 | 5† (45%) | 3 (27%) | 2 (18%) | 1 (5%) |
| Total | 141 | 51 | 50 | 34 | 6 |

*The percentage of patients showing excellent response significantly lower than in the other frequency-at-baseline groups (P = 0.004, Fisher's exact test).
†Including one female patient.

Loxoprofen's effectiveness was also analyzed on the basis of the patients' main diseases and related symptoms to nocturia (Table 3). Of patients with diseases of the prostate, the excellent and improved rates were 39% and 34%, respectively, in 93 with BPH, who were mainly being treated with an alpha-blocker, and 29% and 33%, respectively, in 24 with prostate cancer, of whom 15 were receiving an LH-RH agonist. Loxoprofen was remarkably effective in 13 patients with NB, in whom the excellent and improved response rates were 69% and 89%, respectively (P=0.036 vs results obtained in patients with prostate diseases). Excellent response rates were also high in patients with insomnia (35%) and urinary frequency without urge incontinence (44%). However, excellent rates were low in patients with urinary frequency with urge incontinence (20%) and in those with nocturnal polyuria (14%).

TABLE 3

Efficacy of loxoprofen in nocturia by patients main diseases plus insomnia, urinary frequency, nocturnal polyuria or urge incontinence

| Main Diseases and Symptoms | No. of Patients | Excellent | Improved | Unchanged | Worsened |
|---|---|---|---|---|---|
| BPH | 93 | 36 (39%) | 32 (34%) | 21 (23%) | 4 (4%) |
| Prostatodynia | 5 | 1 (20%) | 2 (40%) | 1 (20%) | 1 (20%) |
| Prostate cancer | 24 | 7 (29%) | 8 (33%) | 8 (33%) | 1 (4%) |
| hormone therapy | 15 | 5 | 3 | 6 | 1 |
| post-radiation | 4 | 1 | 3 | — | — |
| post-prostatectomy* | 5 | 1 | 2 | 2 | — |
| Neurogenic bladder | 13[†] | 9[‡] (69%) | 1[¶] (8%) | 2[¶] (15%) | 1 (8%) |
| Interstitial cystitis | 2[¶] | 2[¶] | | | |
| Insomnia | 20 | 7 (35%) | 8 (40%) | 4 (20%) | 1 (5%) |
| Urinary frequency | | | | | |
| without UUI | 9 | 4[¶] (44%) | 2 (22%) | 2[¶] (22%) | 1 (11%) |
| with UUI | 10 | 2 (20%) | 5[†] (50%) | 3[¶] (30%) | |
| Nocturnal polyuria | 7 | 1 (14%) | 5 (71%) | 1 (14%) | |

*Prostatectomy = radical prostatectomy.
[†]Indicates two patients were female.
[‡]Percentage of patients showing excellent response significantly higher than in the other main disease groups (P = 0.036, Fisher's exact test).
[¶]Indicates one patient was female.
UUI, urge incontinence.

Table 4 shows the effects of loxoprofen in patients who did not respond to previous treatments for nocturia concurrently with therapy for their main diseases. Since almost al of these patients had bladder outlet obstruction (BOO), anticholinergic drugs such as imipramine 10 mg or oxybutynin 2 mg had been administered prior to sleeping. In 108 patients who did nor respond to anticholinergic drugs, the excellent and improved rates of loxoprofen were 44% and 38%, respectively. In 42 patients who did not respond to hypnotics, the excellent and improved rates following loxoprofen therapy were 31% and 38%, respectively. However, excellent effects were obtained only in one of nine patients who previously responded or were refractory to antidiuretic hormone. Loxoprofen was an effective treatment for nocturia in BPH patients who had undergone transurethral resection of the prostate (TURP) or received previous thermotherapy: excellent responses were obtained in 44% of 18 patients with nocturia appearing=2 years after TURP procedures were carried out and in 42% of 19 patients with BPH whose nocturia did not respond to thermotherapy.

TABLE 4

Efficacy of loxoprofen among non-responders to previous treatments for nocturia

| Previous Treatments | No. of Patients | Excellent | Improved | Unchanged | Worsened |
|---|---|---|---|---|---|
| Anticholinergics* | 32 | 14 (44%) | 12 (38%) | 6 (19%) | 1 (3%) |
| TCA[†] | 76 | 30 (39%) | 28 (37%) | 17 (22%) | 4 (5%) |
| Hypnotics | 42 | 13 (31%) | 16 (38%) | 11 (26%) | 2 (5%) |
| Antidiuretic hormone[‡] | | | | | |
| non-responder | 3 | | 1 (33%) | 2 (67%) | |
| responder | 6 | 1 (17%) | 4 (67%) | 1 (17%) | |
| Post-TURP | 18 | 8 (44%) | 5 (27%) | 4 (22%) | 1 (6%) |
| Post-thermotherapy[‡] | 19 | 8 (42%) | 5 (26%) | 6 (32%) | |

*Non-responders to oxybutynin hydrochloride 2 mg, propiverine hydrochloride 10 mg and/or clenbuterol hydrochloride 40 μg administered before sleeping.
[†]Non-responders to imipramine hydrochloride 10 mg and/or amitriptyline hydrochloride administered before sleeping.
[‡]Desmopressin nasal drop.
[‡]Patients who had nocturia for approximately 2 years after TURP.
TCA: tricyclic antidepressants.

After the evaluation, loxoprofen therapy was continued or not according to the patients' wishes (Table 5). Of 101 excellent and improved patients, 11 continued to take loxoprofen every night and 43 when necessary. The improvement of nocturia lasted for several months even after discontinuation of therapy in 11 (10%) who discontinued loxoprofen after 5 to 310 days' administration. In addition, in five patients in whom loxoprofen's effectiveness reduced after continuous administration, the effectiveness recovered with occasional administration following withdrawal for several weeks.

TABLE 5

Continuation and termination of loxoprofen administration after the trial treatment in patients with excellent and improved outcome

| | a) Total Outcome | | | |
|---|---|---|---|---|
| | No. of Patients | Continued administration | Continued occasional Administration | Terminated |
| Excellent (average days) | 51 | 9 (18%) (129) | 26 (51%) (95) | 16 (31%) (56) |
| Improved (average days) | 50 | 2 (4%) (60) | 17 (34%) (54) | 31 (62%) (20) |

TABLE 5-continued

Continuation and termination of loxoprofen administration after the trial treatment in patients with excellent and improved outcome

| Total | 101 | 11 | 43 | 47 |
|---|---|---|---|---| b) Stated Reasons for Discontinuing Therapy

| | No. of Patients with Excellent Response (Mean No. of Prescription Days) | No. of Patients with Improved Response (Mean No. of Prescription Days) |
|---|---|---|
| Cured or stable improvement | 7 (5-310 days/75 days) | 4 (5-42 days/26 days) |
| Stopped visiting clinic | 7 (11-56 days/27 days) | 2 (14, 19 days) |
| Due to adverse events | 1 | 9 (3-28 days/10 days) |
| No worry about nocturia | | 7 (5-21 days/11 days) |
| Too many drugs | — | 3 (7-28 days/15 days) |
| Reduced efficacy | | 2 (35, 119 days) |
| Others (underwent TURP etc) | 1 (30 days) | 4 (21-112 days/49 days) |
| Total | 16 | 31 |

As shown in the above results, nocturia either improved or disappeared in 72% of patients. Considering that the majority of these patients did not respond to treatments for their main diseases nor to anticholinergic drugs and/or hypnotics, the effectiveness of loxoprofen is highly encouraging. Anticholinergic drugs, which are most commonly given to patients with nocturia who do not respond to treatments for LUTS, are not only limited to small doses for patients with BOO and NB, but also frequently cause constipation and dry mouth or thirst. In addition, many elderly patients who receive hypnotics worry about habituation side effects.

One of the main merits of loxoprofen for the treatment of nocturia is that it does not decrease voiding power even in patients with BOO and does not produce side effects such as dry mouth, constipation and habituation. In addition, improvements of nocturia lasted in some patients even after the discontinuation of loxoprofen, and in some patients in whom the effects were reduced during continuous administration, the benefits recovered after switching to occasional administration following withdrawal for several weeks. These results clearly indicate that loxoprofen is highly effective for the treatment of nocturia.

What is claimed is:

1. A method for the treatment of nocturia which consists of administering to a mammal in need of such treatment a therapeutically effective amount of a nonsteroidal anti-inflammatory drug consisting of loxoprofen or a pharmacologically acceptable salt thereof, wherein the mammal is a human who experienced a decrease in the effectiveness of said loxoprofen or a pharmacologically acceptable salt thereof for the treatment of nocturia after continuously being administered with said loxoprofen or a pharmacologically acceptable salt thereof, and then discontinuing the administering of said loxoprofen or a pharmacologically acceptable salt thereof for several weeks and then resuming the administering of said loxoprofen or a pharmacologically acceptable salt thereof whereupon the effectiveness for the treatment of nocturia is recovered.

2. The method according to claim 1, wherein the loxoprofen or a pharmacologically acceptable salt thereof is a pharmacologically acceptable sodium salt of loxoprofen.

* * * * *